(12) United States Patent
Yamada et al.

(10) Patent No.: US 7,993,912 B2
(45) Date of Patent: Aug. 9, 2011

(54) BIOSENSOR CAPABLE OF SIMULTANEOUS DETECTION OF SUBSTRATE BINDING AND REACTION PRODUCT

(75) Inventors: Takayuki Yamada, Tokyo (JP); Toshihide Ezoe, Woodbridge, CT (US); Koji Kuruma, Tokyo (JP)

(73) Assignee: FujiFilm Corporation, Tokyo (JP)

( * ) Notice: Subject to any disclaimer, the term of this patent is extended or adjusted under 35 U.S.C. 154(b) by 0 days.

(21) Appl. No.: 12/203,676

(22) Filed: Sep. 3, 2008

(65) Prior Publication Data
US 2009/0065355 A1    Mar. 12, 2009

(30) Foreign Application Priority Data

Sep. 4, 2007  (JP) ................................ 2007-228689

(51) Int. Cl.
*C12M 1/34*     (2006.01)
(52) U.S. Cl. .................. 435/288.7; 422/82.11; 435/808; 436/164; 436/514; 436/524; 436/525; 436/805
(58) Field of Classification Search .......................... None
See application file for complete search history.

(56) References Cited

U.S. PATENT DOCUMENTS

| 5,071,248 A | 12/1991 | Tiefenthaler et al. |
| 6,498,010 B1 | 12/2002 | Fitzgerald et al. |

FOREIGN PATENT DOCUMENTS

| JP | 2002-148187 A | 5/2002 |
| JP | 2003-232725 A | 8/2003 |
| JP | 2005-024483 A | 1/2005 |
| WO | 92/21768 A1 | 12/1992 |
| WO | 2005/046859 A2 | 5/2005 |

OTHER PUBLICATIONS

Karlsson et al: "Surface Plasmon Resonance Detection and Multispot Sensing for Direct Monitoring of Interactions Involving Low-Molecular-Weight Analytes and for Determination of Low Affinities" Analytical Biochemistry, Academic Press Inc. New York, vol. 228, No. 2, Jan. 1, 1995, pp. 274-280, XP002319706.

(Continued)

*Primary Examiner* — Chris L Chin
(74) *Attorney, Agent, or Firm* — Sughrue Mion, PLLC

(57) ABSTRACT

An object of the present invention is to provide a biosensor that can detect binding of a compound with a functional protein and then assay a reaction product derived from the activity of the functional protein again. The present invention provides a biosensor for detecting a test molecule specifically binding to a physiologically active substance, which comprises; (1) (a) a first reaction region on which the physiologically active substance has been immobilized for performing a binding reaction between the physiologically active substance and the test molecule and a physiologically active reaction caused by the physiologically active substance, and (b) a second reaction region on which a molecule that specifically binds to a reaction product resulting from the physiologically active reaction has been immobilized for performing a binding reaction between the reaction product and the molecule that specifically binds to the reaction product, in the same area; and (2) an assay region for detecting changes in the binding reaction in the first reaction region and in the binding reaction in the second reaction region.

7 Claims, 6 Drawing Sheets

OTHER PUBLICATIONS

Fernandez-Romero J M; Luque De Castro M D: "Flow-through optical biosensor based on the permanent immobilization of an enzyme and transient retention of a reaction product". Analytical Chemistry, vol. 65, No. 21, Nov. 1, 1993, pp. 3048-3052, XP007906613.

Zourob M et al: "Metal clad leaky waveguides for chemical and biosensing applications". Biosensors & Bioelectronics, Elsevier Science Publishers, Barking, GB, vol. 20, No. 9, Mar. 15, 2005, pp. 1718-1727, XP004727593.

Lofas S et al: "Bioanalysis With Surface Plasmon Resonance". Sensors and Actuators B, Elsevier Sequoia S.A., Lausanne, CH, vol. B05, No. 1/04, Aug. 1, 1991, pp. 79-84, XP000265940.

Loefaas S et al: "A Novel Hydrogel Matrix on Gold Surfaces in Surface Plasmon Resonance Sensors for Fast and Efficient Covalent Immobilization of Ligands". Journal of the Chemical Society, Chemical Communications, Chemical Society. Letchworth, GB, No. 21, Jan. 1, 1990, pp. 1526-1528, XP008050238.

An extended European Search Report dated Dec. 23, 2008.

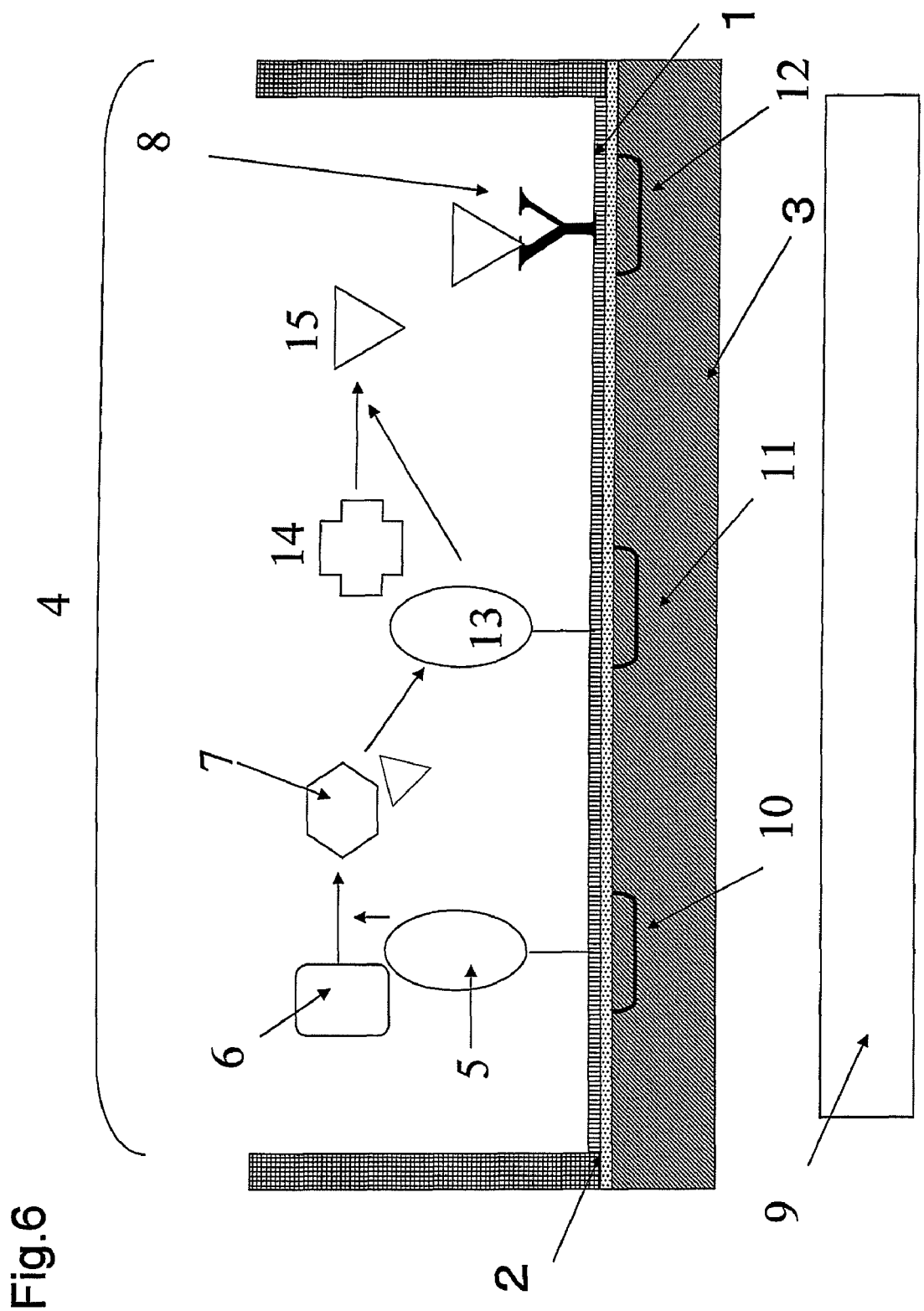

BIOSENSOR CAPABLE OF SIMULTANEOUS DETECTION OF SUBSTRATE BINDING AND REACTION PRODUCT

TECHNICAL FIELD

The present invention relates to a biosensor capable of simultaneous detection of substrate binding and a reaction product.

BACKGROUND ART

As a method for directly detecting a specific reaction without labels, a method for detecting a specific binding based on changed refractive indexes via surface plasmon resonance (SPR) has been put to practical use. This enables specific detection of low-molecular-weight molecules. Thus, such method has been applied to drug screening or used for other applications.

For example, JP Patent Publication (kokai) No. 2002-148187 A discloses a surface plasmon resonance enzyme sensor chip used for a surface plasmon resonance apparatus, which comprises an optically transparent substrate and a thin metal layer of gold or silver formed thereon, the metal thin film being modified with a membrane that undergoes an electron transfer reaction with both the thin metal layer and an enzyme. Also, JP Patent Publication (kokai) No. 2003-232725 A discloses a sensor for analyzing chemical reactions which comprises; a prism; a thin metal layer thereon; a sensor chip comprising a flat micro-fluid channel having a thickness of 30 μm or smaller in which a sample flows while being in direct contact with the surface of the thin metal layer; a light source means for irradiating the back surface of the thin metal layer via total internal reflection through the prism; and a means for measurement allowing the measurement of the spatial distribution of the refractive index of the light reflected from the sensor chip with the elapse of time. A sample is allowed to flow through the flat micro-fluid channel, the spatial distribution of the refractive index resulting from physical or chemical reactions of the sample is measured with the elapse of time, and the reaction rate of physical or chemical reaction of the sample is measured based on the results of measurement.

Many target proteins of drug screening are functional proteins, such as enzymes. In the field of drug discovery, accordingly, it is important to obtain a compound that would influence the activity of functional proteins. When only the binding of a compound to a protein is detected based on SPR signals, however, whether or not its binding is binding to an active site of the protein, binding to another site, or binding to an inactivated protein, could not be determined.

If binding of a compound to a functional protein is detected and a reaction product derived from the activity of the functional protein can then be assayed again, accordingly, whether or not the initial binding of a compound would affect the activity can be determined.

JP Patent Publication (kokai) No. 2005-24483 A discloses a biosensor according to a different concept, which is a biosensor for detecting a molecule associated with specific binding of a biomolecule, which comprises: (i) a reaction region where a) a specific binding reaction and b) an enzyme reaction are performed; (ii) a detection region where a product of an oxidation-reduction reaction resulting from the reactions a) and b) is reacted with a membrane of an oxido-reducing substance; and (iii) an assay region where changes in conditions of the membrane of an oxido-reducing substance resulting from the reaction with a product of an oxidation-reduction reaction are assayed to determine changes in dielectric constant. The invention of JP Patent Publication (kokai) No. 2005-24483 A is intended to provide a biosensor that can provide amplification effects via an enzyme in a micro-fluid channel. According to a highly-sensitive assay technique employing a specific binding reaction and enzyme amplification, a membrane that captures a product of an enzyme reaction at a site downstream of a micro-fluid channel is provided, and the progress of such capture is assayed by measuring the dielectric constant of the membrane, so that the effects of enzyme amplification can be realized without restriction regarding the volume of the fluid channel, even when a substrate continuously flows through the micro-fluid channel. Thus, a lower limit of detection in terms of concentration can be achieved. With the use of such biosensor, however, reaction products are limited to products of oxidation-reduction reactions. Accordingly, such sensor cannot be applied to the evaluation of the binding of a compound to any type of functional protein.

DISCLOSURE OF THE INVENTION

An object of the present invention is to overcome the drawbacks of conventional techniques described above. Specifically, an object of the present invention is to provide a biosensor that can detect binding of a compound with a functional protein and then assay a reaction product derived from the activity of the functional protein again.

The present inventors have conducted concentrated studies in order to attain the above object. As a result, they discovered that a biosensor that can attain the above object could be obtained by providing, in the same area, a first reaction region on which a physiologically active substance has been immobilized and a second reaction region on which a molecule that specifically binds to a product resulting from a physiologically active reaction caused by the aforementioned physiologically active substance has been immobilized. This has led to the completion of the present invention.

Thus, the present invention provides a biosensor for detecting a test molecule specifically binding to a physiologically active substance, which comprises;
(1) (a) a first reaction region on which the physiologically active substance has been immobilized for performing a binding reaction between the physiologically active substance and the test molecule and a physiologically active reaction caused by the physiologically active substance, and (b) a second reaction region on which a molecule that specifically binds to a reaction product resulting from the physiologically active reaction has been immobilized for performing a binding reaction between the reaction product and the molecule that specifically binds to the reaction product, in the same area; and
(2) an assay region for detecting changes in the binding reaction in the first reaction region and in the binding reaction in the second reaction region.

Preferably, the biosensor of the present invention comprises two or more first reaction regions.

Preferably, the biosensor of the present invention comprises two or more second reaction regions.

Preferably, the first reaction region and the second reaction region are separated from each other by an air gap.

Preferably, the air gap is movable air gap.

Preferably, the changes in the binding reaction in the first reaction region and in the binding reaction in the second reaction region are changes in dielectric constant.

Preferably, the assay region is a waveguide.

With the use of the biosensor of the present invention, binding of a compound to a functional protein can be first detected, a reaction product derived from the activity of the functional protein can then be assayed again, and the reaction can be detected without labels or fluorescence. With the use of the biosensor of the present invention, binding to a functional protein and influences on activity can be simultaneously detected without labels or fluorescence.

BRIEF DESCRIPTION OF THE DRAWINGS

FIG. 6 schematically shows another embodiment of the biosensor of the present invention.

Figure 1:
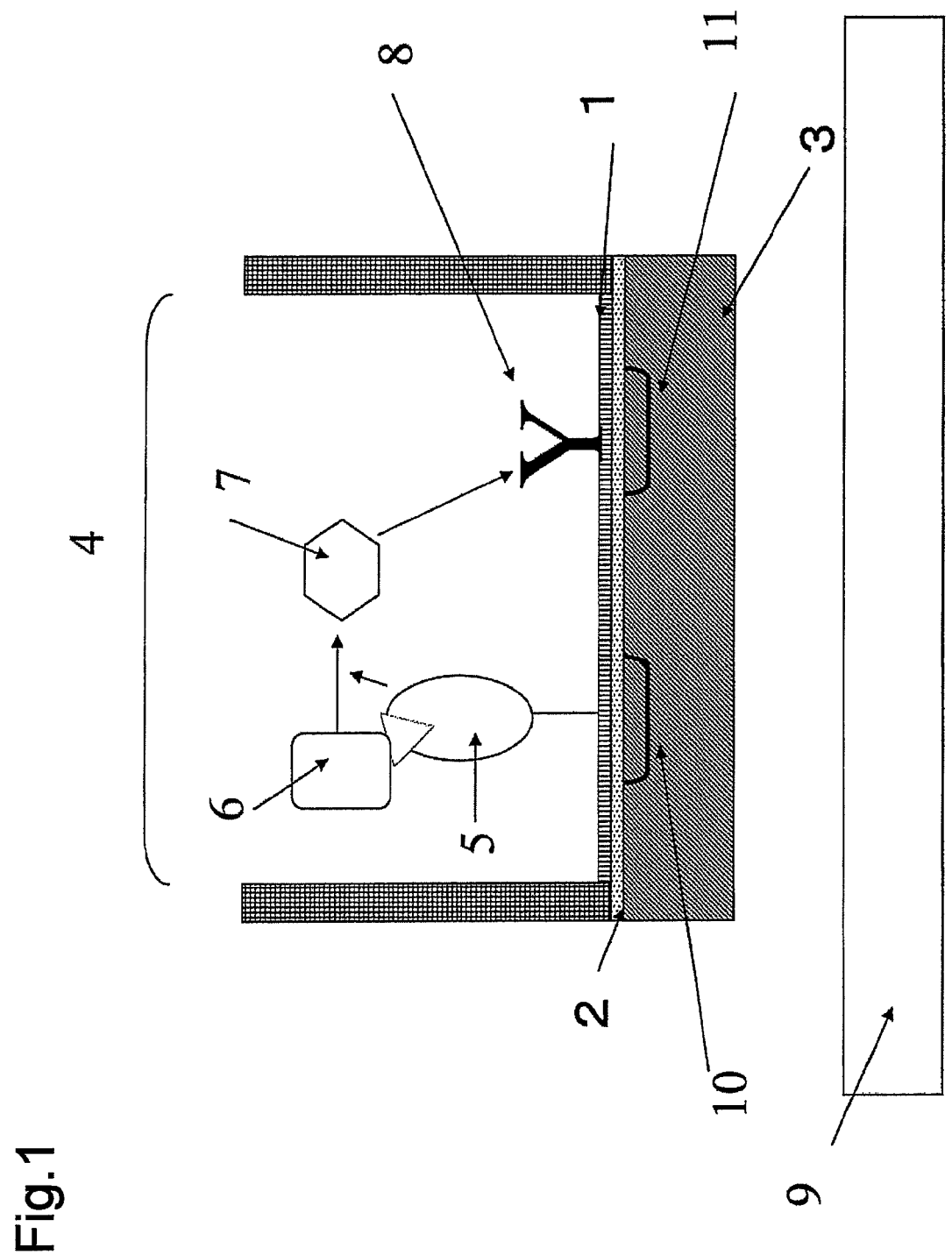
FIG. 1 schematically shows an embodiment of the biosensor of the present invention.

In Figures, 1 represents hydrophilic film, 2 represents gold thin-film substrate, 3 represents prism, 4 represents reaction region, 5 represents enzyme, 6 represents substrate, 7 represents reaction product, 8 represents specific binding molecule, 9 represents assay apparatus, 10 represents immobilization region, 11 represents immobilization region, 12 represents immobilization region, 13 represents enzyme, 14 represents substrate, and 15 represents reaction product.

BEST MODES FOR CARRYING OUT THE INVENTION

Hereafter, the embodiments of the present invention are described in detail.

The biosensor of the present invention is a biosensor for detecting a test molecule specifically binding to a physiologically active substance, which comprises;
(1) (a) a first reaction region on which the physiologically active substance has been immobilized for performing a binding reaction between the physiologically active substance and the test molecule and a physiologically active reaction caused by the physiologically active substance, and (b) a second reaction region on which a molecule that specifically binds to a reaction product resulting from the physiologically active reaction has been immobilized for performing a binding reaction between the reaction product and the molecule that specifically binds to the reaction product, in the same area; and
(2) an assay region for detecting changes in the binding reaction in the first reaction region and in the binding reaction in the second reaction region.

The biosensor of the present invention has as broad a meaning as possible, and the term biosensor is used herein to mean a sensor, which converts an interaction between biomolecules into a signal such as an electric signal, so as to measure or detect a target substance. The conventional biosensor is comprised of a receptor site for recognizing a chemical substance as a detection target and a transducer site for converting a physical change or chemical change generated at the site into an electric signal. In a living body, there exist substances having an affinity with each other, such as enzyme/substrate, enzyme/coenzyme, antigen/antibody, or hormone/receptor. The biosensor operates on the principle that a substance having an affinity with another substance is immobilized on a substrate to be used as a molecule-recognizing substance, so that the corresponding substance can be selectively measured.

The number of first reaction regions is not particularly limited. A single first reaction region or two or more first reaction regions may be provided. Also, the number of second reaction regions is not particularly limited. A single second reaction region or two or more second reaction regions may be provided. In the case of existing biosensors, it has been difficult to independently carry out reactions in each reaction region, when several reaction regions were collectively present. This also increases the size of the sensor, which would disadvantageously lead to increased cost or loss of a sample.

The first reaction region is preferably separated from the second reaction region. The first reaction region is preferably separated from the second reaction region by air gap. An air gap may be movable. When separation by means of an air gap has been intended, it has been difficult to maintain the size of the air gap at a constant level and to accurately fix the position thereof. Thus, it has been difficult to use an air gap to separate a liquid in the reaction region of the biosensor.

The substrate for immobilizing a physiologically active substance which is used in the present invention is preferably a metal surface or a metal film. A metal constituting the metal surface or metal film is not particularly limited, as long as surface plasmon resonance is generated when the metal is used for a surface plasmon resonance biosensor. Examples of a preferred metal may include free-electron metals such as gold, silver, copper, aluminum or platinum. Of these, gold is particularly preferable. These metals can be used singly or in combination. Moreover, considering adherability to the above carrier, an interstitial layer consisting of chrome or the like may be provided between the carrier and a metal layer.

The film thickness of a metal film is not limited. When the metal film is used for a surface plasmon resonance biosensor, the thickness is preferably between 0.1 nm and 500 nm, and particularly preferably between 1 nm and 200 nm. If the thickness exceeds 500 nm, the surface plasmon phenomenon of a medium cannot be sufficiently detected. Moreover, when an interstitial layer consisting of chrome or the like is provided, the thickness of the interstitial layer is preferably between 0.1 nm and 10 nm.

Formation of a metal film may be carried out by common methods, and examples of such a method may include sputtering method, evaporation method, ion plating method, electroplating method, and nonelectrolytic plating method.

The metal film is preferably placed on a substrate. The description "placed on a substrate" is used herein to mean a case where a metal film is placed on a substrate such that it directly comes into contact with the substrate, as well as a case where a metal film is placed via another layer without directly coming into contact with the substrate. When a substrate of the present invention is used for a surface plasmon resonance biosensor, examples of a substrate may include, generally, optical glasses such as BK7, and synthetic resins. More specifically, materials transparent to laser beams, such as polymethyl methacrylate, polyethylene terephthalate, polycarbonate or a cycloolefin polymer, can be used. For such a substrate, materials that are not anisotropic with regard to polarized light and have excellent workability are preferably used.

The substrate in the present invention is preferably a substrate which was coated with a hydrophilic polymer having a reactive group. The hydrophilic polymer having a reactive group can be bound to the above-described metal surface or metal film directly or via an intermediate layer.

Examples of a hydrophilic polymer compound include polysaccharides (e.g., agarose, dextran, carrageenan, alginic acid, starch, and cellulose) and synthetic polymer compounds (e.g., polyvinyl alcohol). In the present invention, a polysaccharide is preferably used, and dextran is most preferably used.

In the present invention, preferably, a hydrophilic polymer with an average molecular weight of 10,000 to 2,000,000 can be used. Preferably, a hydrophilic polymer with an average molecular weight of 20,000 to 2,000,000, further preferably 30,000 to 1,000,000, and most preferably 200,000 to 800,000 can be used.

A hydrophilic polymer which is immobilized on the surface of a sensor preferably has a thickness between 1 and 300 nm in an aqueous solution. If the film thickness is too small, the quantities of physiologically active substances immobilized are reduced. In addition, since a hydration layer on the sensor surface becomes thin, physiologically active substances denature by themselves, and it thereby becomes difficult to detect the interaction of such physiologically active substances with test substances. On the other hand, if the film thickness is too large, it impairs dispersions of test substances in the film. Moreover, in particular, when such interaction is detected from the side opposite to the surface of a sensor substrate on which a hydrophilic polymer is immobilized, the distance between a detection surface and an interaction-forming portion is increased, resulting in a decrease in detection sensitivity. The film thickness of a hydrophilic polymer in an aqueous solution can be evaluated by AFM, ellipsometry measurement, etc.

A polyhydroxy compound that is an example of the hydrophilic polymer can be carboxylated by reacting the compound with bromoacetic acid under basic conditions, for example. Through control of the reaction conditions, a given proportion of hydroxy groups contained in the polyhydroxy compound in its initial state can be carboxylated. In the present invention, 1% to 90% of hydroxy groups can be carboxylated, for example. In addition, the degree of carboxylation (% carboxylation) on a surface coated with any polyhydroxy polymer compound can be calculated by the following method, for example. The film surface is subjected to gas-phase modification at 50° C. for 16 hours using di-tert-butyl carbodiimide/pyridine catalyst and trifluoroethanol. A fluorine amount derived from trifluoroethanol is measured via ESCA (electron spectroscopy for chemical analysis). The ratio of the fluorine amount to an oxygen amount on the film surface (hereinafter, referred to as an F/O value) is then calculated. The theoretical F/O value when all the hydroxy groups are carboxylated is determined to represent 100% carboxylation. The F/O value resulting when carboxylation is performed under arbitrary conditions is measured and then the degree of carboxylation (% carboxylation) at this time can be calculated.

An approach known in the art, for example, a method comprising performing activation with 1-(3-Dimethylaminopropyl)-3 ethylcarbodiimide (EDC) as water-soluble carbodiimide and N-Hydroxysuccinimide (NHS), or a method comprising performing activation with EDC alone, can be used preferably as a method of activating the polymer containing a carboxyl group. The polymer containing the carboxyl group activated by this approach can be reacted with the substrate having an amino group to thereby produce the biosensor of the present invention.

The reaction group introduced into a polymer as a group for immobilizing a physiologically active substance may be a carboxyl group or an amino group. Also, a state is also possible in which a physiologically active substance such as a biotin-binding protein (such as avidin, streptavidin, or neutravidin), Protein A, Protein G, an antigen, or an antibody (for example, a known tag antibody such as an anti-GST antibody) is previously immobilized. A physiologically active substance having a membrane structure such as a lipid, can be immobilized by using an immobilization layer of a polymer to which alkane is introduced. According to an application purpose, the length of a polymer chain, the thickness of a polymer, the density of a polymer, or the amount of a reaction group to be introduced into a polymer is controlled. As a result, it is possible to be applied to various types of protein. Furthermore, a His-tag ligand or the like can be immobilized through a metal chelate by introducing NTA (nitrilotriacetic acid) or the like as an immobilization group into a polymer.

In the present invention, a hydrophilic polymer having reactive groups can be bound directly to a metal surface or a metal film or indirectly via an intermediate layer. As such "intermediate layer" used herein, a layer comprising a hydrophobic polymer compound or a self-assembled membrane can be used, for example. Hereinafter, the hydrophobic polymer compound and the self-assembled membrane will be explained.

The hydrophobic polymer compound is a polymer compound lacking water-absorbing properties and having solubility (25° C.) in water of 10% or less, more preferably 1% or less, and most preferably, 0.1% or less.

Hydrophobic monomers that form such hydrophobic polymer compound can be arbitrarily selected from among vinyl esters, acrylic acid esters, methacrylic acid esters, olefins, styrenes, crotonic acid esters, itaconic acid diesters, maleic acid diesters, fumaric acid diesters, allyl compounds, vinyl ethers, vinyl ketones, and the like. Such hydrophobic polymer compound may be a homopolymer comprising one type of monomer, or a copolymer comprising two or more types of monomer.

Examples of such hydrophobic polymer compound that is preferably used in the present invention include polystyrene, polyethylene, polypropylene, polyethylene terephthalate, polyvinylchloride, polymethyl methacrylate, polyester, and nylon.

A carrier can be coated with such hydrophobic polymer compound by a conventional method such as spin coating, air-knife coating, bar coating, blade coating, slide coating, or curtain coating. Coating can also be performed by a spray method, an evaporation method, a cast method, a dipping method, or the like.

The coating thickness of the hydrophobic polymer compound is not particularly limited and is preferably 0.1 nm to 500 nm, and particularly preferably 1 nm to 300 nm.

Next, the self-assembled membrane will be explained. Sulfur compounds such as thiol and disulfides are spontaneously adsorbed onto a noble metal (e.g., gold) substrate, so that a monomolecular-sized ultra-thin film can be produced. A cluster of such sulfur compounds has a sequence depending on the crystal lattice of a substrate or the molecular structure of the adsorbed molecules. Hence, the thus provided membrane is referred to as a self-assembled membrane. Specifically, in the present invention, a hydrophilic polymer can be adhered to a metal film via an organic molecule $X^1$—$R^1$—$Y^1$. The organic molecule $X^1$—$R^1$—$Y^1$ will be described in detail.

$X^1$ is a group having binding affinity for a metal film. Specifically, asymmetric or symmetric sulfide (—$SSR^{11}Y^{11}$, —$SSR^1Y^1$), sulfide (—$SR^{11}Y^{11}$, —$SR^1Y^1$), diselenide (—$SeSeR^{11}Y^{11}$, —$SeSeR^1Y^1$), selenide ($SeR^{11}Y^{11}$, —$SeR^1Y^1$), thiol (—SH), nitrile (—CN), isonitrile, nitro (—$NO_2$), selenol (—SeH), a trivalent phosphorus compound, isothiocyanate, xanthate, thiocarbamate, phosphine, thio acid, or dithioic acid (—COSH, —CSSH) is preferably used.

$R^1$ (and $R^{11}$) is occasionally interrupted via hetero atoms, is preferably linear (unbranched) because of appropriately dense packing, and is occasionally a hydrocarbon chain containing double and/or triple bonds. The length of the chain is preferably 10 or more atoms. The carbon chain can be occasionally perfluorinated.

$Y^1$ and $Y^{11}$ are groups for binding with a polyhydroxy polymer compound. $Y^1$ and $Y^{11}$ are preferably the same and are capable of binding directly with such polyhydroxy polymer compound or binding with the same after activation. Specifically, a hydroxyl, carboxyl, amino, aldehyde, hydrazide, carbonyl, epoxy, or vinyl group can be used, for example.

In the present invention, 7-carboxy-1-heptanethiol, 10-carboxy-1-decanethiol, 4,4'-dithiodibutyric acid, 11-hydroxy-1-undecanethiol, 11-amino-1-undecanethiol, and the like can be used as self-assembled compounds, for example.

In the present invention, a metal film is covered with an organic layer having an amino group, and then the organic layer is reacted with a polymer having an activated carboxyl group. Thus, a hydrogel capable of immobilizing a physiologically active substance can be produced.

In the present invention, a known method can be used as a method for coating a metal film with an organic layer having an amino group. In view of simple operation, a method for coating with the use of a self-assembled membrane (SAMs) is preferred. A method for coating a metal film with the use of a self-assembled membrane (SAMs) has been actively developed by Professor Whitesides et al. (Harvard University). Details of the method are reported in, for example, Chemical Review, 105, 1103-1169 (2005). When gold is used as a metal, an orientational self-assembled monomolecular film is formed with the use of an alkanethiol derivative represented by the following formula A-1 (in the formula A-1, n represents an integer from 3 to 20, and X represents a functional group) as an organic layer-forming compound based on the van der Waals force between an Au—S bond and an alkyl chain. A self-assembled membrane is formed by a very simple method, wherein a gold substrate is immersed in a solution of an alkanethiol derivative. A self-assembled membrane is formed with the use of a compound represented by the following formula A-1 where X is $NH_2$, so that it becomes possible to coat a gold surface with an organic layer comprising an amino group:

$$HS(CH_2)_nX \quad\quad\quad A\text{-}1$$

An alkanethiol having an amino group at the end may be a compound comprising a thiol group and an amino group linked via an alkyl chain (formula A-2) (in the formula A-2, n represents an integer of 3 to 20), or may be a compound obtained by reaction between alkanethiol having a carboxyl group at the end (formula A-3 or A-4) (in the formula A-3, n represents an integer of 3 to 20, and in the formula A-4, n each independently represents an integer of 1 to 20) and a large excess of hydrazide or diamine. The reaction between alkanethiol having a carboxyl group at the end and a large excess of hydrazide or diamine may be performed in a solution state. Alternatively, the alkanethiol having a carboxyl group at the end may be bound to the substrate surface and then reacted with a large excess of hydrazide or diamine.

$$HS(CH_2)_nNH_2 \quad\quad\quad A\text{-}2$$

$$HS(CH_2)_nCOOH \quad\quad\quad A\text{-}3$$

$$HS(CH_2)_n(OCH_2CH_2)_nOCH_2COOH \quad\quad\quad A\text{-}4$$

The repeating number of alkyl group of the formulas A-2 to A-4 is preferably 3 to 20, more preferably 3 to 16, and most preferably 4 to 8. If the alkyl chain is short, formation of self-assembled membrane becomes difficult, and if the alkyl chain is long, water solubility decreases and the handling becomes difficult.

Any compound may be used as the diamine used in the present invention. An aqueous diamine is preferable for use in the biosensor surface. Specific examples of the aqueous diamine may include aliphatic diamine such as ethylenediamine, tetraethylenediamine, octamethylenediamine, decamethylenediamine, piperazine, triethylenediamine, diethylenetriamine, triethylenetetraamine, dihexamethylenetriamine, and 1,4-diaminocyclohexane, and aromatic diamine such as paraphenylenediamine, metaphenylenediamine, paraxylylenediamine, metaxylylenediamine, 4,4'-diaminobiphenyl, 4,4'-diaminodiphenylmethane, 4,4'-diaminodiphenylketone, and 4,4'-diaminodiphenylsulfonic acid. From the viewpoint of increasing the hydrophilicity of the biosensor surface, a compound comprising two amino groups linked via an ethylene glycol unit (formula A-5) may also be used. The diamine used in the present invention is preferably ethylenediamine or the compound represented by the formula A-5 (in the formula A-5 n and m each independently represent an integer of 1 to 20), more preferably ethylenediamine or 1,2-bis(aminoethoxy)ethane (represented by the formula A-5 wherein n=2 and m=1).

$$H_2N(CH_2)_n(OCH_2CH_2)_mO(CH_2)_nNH_2 \quad\quad\quad A\text{-}5$$

The alkanethiol having an amino group may form a self-assembled membrane by itself or may form a self-assembled membrane by mixing it with another alkanethiol. It is preferred for use in the biosensor surface that a compound capable of suppressing the nonspecific adsorption of a physiologically active substance should be used as the another alkanethiol. The aforementioned Professor Whitesides et al. have investigated in detail self-assembled membrane capable of suppressing the nonspecific adsorption of a physiologically active substance and have reported that a self-assembled membrane formed from alkanethiol having a hydrophilic group is effective for suppressing nonspecific adsorption (Langmuir, 17, 2841-2850, 5605-5620, and 6336-6343 (2001)). In the present invention, any of compounds described in the aforementioned papers may be used preferably as the alkanethiol that forms a mixed monolayer with an alkanethiol having an amino group. In terms of excellent ability to suppress nonspecific adsorption and ease of acquisition, it is preferred that alkanethiol having a hydroxyl group (formula A-6) or alkanethiol having an ethylene glycol unit (formula A-7) (in the formula A-6, n represents an integer of 3 to 20, and in the formula A-7, n and m each independently represent an integer of 1 to 20) should be used as the alkanethiol that forms a mixed monolayer with an alkanethiol having an amino group.

$$HS(CH_2)_nOH \quad\quad\quad A\text{-}6$$

$$HS(CH_2)_n(OCH_2CH_2)_mOH \quad\quad\quad A\text{-}7$$

When alkane thiol having an amino group is mixed with another alkane thiol to form a self-assembled membrane, the repeating number of alkyl group of the formulas A-2 to A-4 is preferably 4 to 20, more preferably 4 to 16, and most preferably 4 to 10. Further, the repeating number of alkyl group of the formulas A-6 and A-7 is preferably 3 to 16, more preferably 3 to 12, and most preferably 3 to 8.

In the present invention, it is possible to mix alkanethiol having an amino group and alkanethiol having a hydrophilic group at an arbitrary ratio. However, when the content of alkanethiol having an amino group is low, the amount of actively esterified carboxyl group-containing polymer to be bound decreases. When the content of alkanethiol having a hydrophilic group is low, the capacity for suppression of nonspecific adsorption is reduced. Thus, the mixing ratio of alkanethiol having an amino group to alkanethiol having a hydrophilic group is preferably 1:1 to 1:1,000,000, more preferably 1:4 to 1:10,000, and further preferably 1:10 to 1:1,000. In view of reduction of steric hindrance upon a reaction with an actively esterified carboxyl group-containing polymer, the molecular length of alkanethiol having an amino group is preferably longer than that of alkanethiol having a hydrophilic group.

As alkanethiol used for the present invention, compounds synthesized based on Abstract, Curr. Org. Chem., 8, 1763-1797 (2004) (Professor Grzybowski, Northwestern University) and references cited therein or a commercially available compound may be used. It is possible to purchase such compounds from Dojindo Laboratories, Aldrich, SensoPath Technologies, Frontier Scientific Inc., and the like. In the present invention, disulfide compounds that are oxidation products of alkanethiol can be used in the same manner as alkanethiol.

A physiologically active substance immobilized on the substrate in the present invention is not particularly limited, as long as it interacts with a measurement target and can show physiologically active reaction. Examples of such a substance may include an immune protein, an enzyme, a microorganism, nucleic acid, a low molecular weight organic compound, a nonimmune protein, an immunoglobulin-binding protein, a sugar-binding protein, a sugar chain recognizing sugar, fatty acid or fatty acid ester, and polypeptide or oligopeptide having a ligand-binding ability.

Examples of an immune protein may include an antibody whose antigen is a measurement target, and a hapten. Examples of such an antibody may include various immunoglobulins such as IgG, IgM, IgA, IgE or IgD. More specifically, when a measurement target is human serum albumin, an anti-human serum albumin antibody can be used as an antibody. When an antigen is an agricultural chemical, pesticide, methicillin-resistant *Staphylococcus aureus*, antibiotic, narcotic drug, cocaine, heroin, crack or the like, there can be used, for example, an anti-atrazine antibody, anti-kanamycin antibody, anti-metamphetamine antibody, or antibodies against O antigens 26, 86, 55, 111 and 157 among enteropathogenic *Escherichia coli*.

An enzyme used as a physiologically active substance herein is not particularly limited, as long as it exhibits an activity to a measurement target or substance metabolized from the measurement target. Various enzymes such as oxidoreductase, hydrolase, isomerase, lyase or synthetase can be used. More specifically, when a measurement target is glucose, glucose oxidase is used, and when a measurement target is cholesterol, cholesterol oxidase is used. Moreover, when a measurement target is an agricultural chemical, pesticide, methicillin-resistant *Staphylococcus aureus*, antibiotic, narcotic drug, cocaine, heroin, crack or the like, enzymes such as acetylcholine esterase, catecholamine esterase, noradrenalin esterase or dopamine esterase, which show a specific reaction with a substance metabolized from the above measurement target, can be used.

A microorganism used as a physiologically active substance herein is not particularly limited, and various microorganisms such as *Escherichia coli* can be used.

As nucleic acid, those complementarily hybridizing with nucleic acid as a measurement target can be used. Either DNA (including cDNA) or RNA can be used as nucleic acid. The type of DNA is not particularly limited, and any of native DNA, recombinant DNA produced by gene recombination and chemically synthesized DNA may be used.

As a low molecular weight organic compound, any given compound that can be synthesized by a common method of synthesizing an organic compound can be used.

A nonimmune protein used herein is not particularly limited, and examples of such a nonimmune protein may include avidin (streptoavidin), biotin, and a receptor.

Examples of an immunoglobulin-binding protein used herein may include protein A, protein G, and a rheumatoid factor (RF).

As a sugar-binding protein, for example, lectin is used.

Examples of fatty acid or fatty acid ester may include stearic acid, arachidic acid, behenic acid, ethyl stearate, ethyl arachidate, and ethyl behenate.

When the physiologically active substance is a protein such as an antibody or an enzyme, or a nucleic acid, the immobilization can be carried out by covalently binding the physiologically active substance to a reactive group on a substrate with the use of amino group, thiol group or the like of the physiologically active substance.

Examples of test molecules are not particularly limited, provided that such molecules interact with the above-mentioned physiologically active substances. Examples of preferable test molecules that can be used include molecules that interact with physiologically active substances, and activate its activity or inhibit activity of such physiologically active substances.

In the present invention, the type of "molecules that specifically bind to products resulting from physiologically active reaction" immobilized in the second reaction region is not particularly limited. An example is an antibody that reacts with a reaction product.

The analysis using the biosensor of the present invention can be performed by using commercially available measurement apparatus. For example, in the case of SPR analysis, Biacore3000, 2000, 1000, A100, T100, S51, X, J (GE Healthcare (Biacore)), SPR-670 and SPR-MACS (Moritex corporation), MulriSPRinter (TOYOBO), and SPR Imager (GWC Technologies) can be used. Further, Epic System (Corning Inc.), AnaLight (Farfield Scientific), AFFINIX (ULVAC Co. (Initium) and the like can be used. Further, the device described on paragraphs 0025-0062 of Japanese Patent Publication (Kokai) No. 2006-194624 can also be used.

In the present invention, a binding reaction in the first reaction region and a binding reaction in the second reaction region are preferably detected and/or assayed by a nonelectrochemical method. Examples of nonelectrochemical methods include surface plasmon resonance (SPR) assay, quartz crystal microbalance (QCM) oscillation assay, and assay techniques involving the use of functionalized surfaces of particles, ranging from gold colloid particles to ultrafine particles. In the present invention, preferably, changes in the binding reaction in the first reaction region and in the binding reaction in the second reaction region can be assayed as changes in dielectric constant.

In a preferred embodiment of the present invention, the biosensor can be used as a biosensor for surface plasmon resonance which is characterized in that it comprises a metal film placed on a transparent substrate.

A biosensor for surface plasmon resonance is a biosensor used for a surface plasmon resonance biosensor, meaning a member comprising a portion for transmitting and reflecting light emitted from the sensor and a portion for immobilizing a physiologically active substance. It may be fixed to the main body of the sensor or may be detachable.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light.

A device using a system known as the Kretschmann configuration is an example of a surface plasmon measurement device for analyzing the properties of a substance to be measured using a phenomenon whereby a surface plasmon is excited with a lightwave (for example, paragraph 0011 of Japanese Patent Laid-Open No. 6-167443). The surface plasmon measurement device using the above system basically comprises a dielectric block formed in a prism state, a metal film that is formed on a face of the dielectric block and comes into contact with a measured substance such as a sample solution, a light source for generating a light beam, an optical system for allowing the above light beam to enter the dielectric block at various angles so that total reflection conditions can be obtained at the interface between the dielectric block and the metal film, and a light-detecting means for detecting the state of surface plasmon resonance, that is, the state of attenuated total reflection, by measuring the intensity of the light beam totally reflected at the above interface.

In order to achieve various incident angles as described above, a relatively thin light beam may be caused to enter the above interface while changing an incident angle. Otherwise, a relatively thick light beam may be caused to enter the above interface in a state of convergent light or divergent light, so that the light beam contains components that have entered therein at various angles. In the former case, the light beam whose reflection angle changes depending on the change of the incident angle of the entered light beam can be detected with a small photodetector moving in synchronization with the change of the above reflection angle, or it can also be detected with an area sensor extending along the direction in which the reflection angle is changed. In the latter case, the light beam can be detected with an area sensor extending to a direction capable of receiving all the light beams reflected at various reflection angles.

With regard to a surface plasmon measurement device with the above structure, if a light beam is allowed to enter the metal film at a specific incident angle greater than or equal to a total reflection angle, then an evanescent wave having an electric distribution appears in a measured substance that is in contact with the metal film, and a surface plasmon is excited by this evanescent wave at the interface between the metal film and the measured substance. When the wave vector of the evanescent light is the same as that of a surface plasmon and thus their wave numbers match, they are in a resonance state, and light energy transfers to the surface plasmon. Accordingly, the intensity of totally reflected light is sharply decreased at the interface between the dielectric block and the metal film. This decrease in light intensity is generally detected as a dark line by the above light-detecting means. The above resonance takes place only when the incident beam is p-polarized light. Accordingly, it is necessary to set the light beam in advance such that it enters as p-polarized light.

If the wave number of a surface plasmon is determined from an incident angle causing the attenuated total reflection (ATR), that is, an attenuated total reflection angle ($\theta$SP), the dielectric constant of a measured substance can be determined. As described on paragraphs 0025-0037 of Japanese Patent Laid-Open No. 11-326194, a light-detecting means in the form of an array is considered to be used for the above type of surface plasmon measurement device in order to measure the attenuated total reflection angle ($\theta$SP) with high precision and in a large dynamic range. This light-detecting means comprises multiple photo acceptance units that are arranged in a certain direction, that is, a direction in which different photo acceptance units receive the components of light beams that are totally reflected at various reflection angles at the above interface.

In the above case, there is established a differentiating means for differentiating a photodetection signal outputted from each photo acceptance unit in the above array-form light-detecting means with regard to the direction in which the photo acceptance unit is arranged. An attenuated total reflection angle ($\theta$SP) is then specified based on the derivative value outputted from the differentiating means, so that properties associated with the refractive index of a measured substance are determined in many cases.

In addition, a leaking mode measurement device described in "Bunko Kenkyu (Spectral Studies)" Vol. 47, No. 1 (1998), pp. 21 to 23 and 26 to 27 has also been known as an example of measurement devices similar to the above-described device using attenuated total reflection (ATR). This leaking mode measurement device basically comprises a dielectric block formed in a prism state, a clad layer that is formed on a face of the dielectric block, a light wave guide layer that is formed on the clad layer and comes into contact with a sample solution, a light source for generating a light beam, an optical system for allowing the above light beam to enter the dielectric block at various angles so that total reflection conditions can be obtained at the interface between the dielectric block and the clad layer, and a light-detecting means for detecting the excitation state of waveguide mode, that is, the state of attenuated total reflection, by measuring the intensity of the light beam totally reflected at the above interface.

In the leaking mode measurement device with the above structure, if a light beam is caused to enter the clad layer via the dielectric block at an incident angle greater than or equal to a total reflection angle, only light having a specific wave number that has entered at a specific incident angle is transmitted in a waveguide mode into the light wave guide layer, after the light beam has penetrated the clad layer. Thus, when the waveguide mode is excited, almost all forms of incident light are taken into the light wave guide layer, and thereby the state of attenuated total reflection occurs, in which the intensity of the totally reflected light is sharply decreased at the above interface. Since the wave number of a waveguide light depends on the refractive index of a measured substance placed on the light wave guide layer, the refractive index of the measurement substance or the properties of the measured substance associated therewith can be analyzed by determining the above specific incident angle causing the attenuated total reflection.

In this leaking mode measurement device also, the above-described array-form light-detecting means can be used to detect the position of a dark line generated in a reflected light due to attenuated total reflection. In addition, the above-described differentiating means can also be applied in combination with the above means.

The above-described surface plasmon measurement device or leaking mode measurement device may be used in random screening to discover a specific substance binding to a desired sensing substance in the field of research for development of new drugs or the like. In this case, a sensing substance is immobilized as the above-described measured substance on the above thin film layer (which is a metal film in the case of a surface plasmon measurement device, and is a clad layer and a light guide wave layer in the case of a leaking mode measurement device), and a sample solution obtained by dissolving various types of test substance in a solvent is added to the sensing substance. Thereafter, the above-described attenuated total reflection angle (θSP) is measured periodically when a certain period of time has elapsed.

If the test substance contained in the sample solution is bound to the sensing substance, the refractive index of the sensing substance is changed by this binding over time. Accordingly, the above attenuated total reflection angle (θSP) is measured periodically after the elapse of a certain time, and it is determined whether or not a change has occurred in the above attenuated total reflection angle (θSP), so that a binding state between the test substance and the sensing substance is measured. Based on the results, it can be determined whether or not the test substance is a specific substance binding to the sensing substance. Examples of such a combination between a specific substance and a sensing substance may include an antigen and an antibody, and an antibody and an antibody. More specifically, a rabbit anti-human IgG antibody is immobilized as a sensing substance on the surface of a thin film layer, and a human IgG antibody is used as a specific substance.

It is to be noted that in order to measure a binding state between a test substance and a sensing substance, it is not always necessary to detect the angle itself of an attenuated total reflection angle (θSP). For example, a sample solution may be added to a sensing substance, and the amount of an attenuated total reflection angle (θSP) changed thereby may be measured, so that the binding state can be measured based on the magnitude by which the angle has changed. When the above-described array-form light-detecting means and differentiating means are applied to a measurement device using attenuated total reflection, the amount by which a derivative value has changed reflects the amount by which the attenuated total reflection angle (θSP) has changed. Accordingly, based on the amount by which the derivative value has changed, a binding state between a sensing substance and a test substance can be measured (Japanese Patent Publication (Kokai) No. 2003-172694 filed by the present applicant). In a measuring method and a measurement device using such attenuated total reflection, a sample solution consisting of a solvent and a test substance is added dropwise to a cup- or petri dish-shaped measurement chip wherein a sensing substance is immobilized on a thin film layer previously formed at the bottom, and then, the above-described amount by which an attenuated total reflection angle (θSP) has changed is measured.

Moreover, Japanese Patent Laid-Open No. 2001-330560 describes a measurement device using attenuated total reflection, which involves successively measuring multiple measurement chips mounted on a turntable or the like, so as to measure many samples in a short time.

The biosensor of the present invention can be used as a biosensor, which has a waveguide structure on the surface of a carrier, for example, and which detects refractive index changes using such a waveguide. In this case, the waveguide structure on the carrier surface has a diffraction grating, and in some cases, an additional layer. This waveguide structure is a planar waveguide body comprising a thin dielectric layer. Light gathered to the waveguide body form is introduced into such a thin layer by total internal reflection. The transmission velocity of the thus introduced light wave (hereinafter referred to as "mode") is indicated as a C/N value. Herein, C indicates the velocity of light in a vacuum, and N indicates an effective refractive index of the mode introduced into the waveguide body. Such an effective refractive index N is determined based on the structure of the waveguide body on one face, and is determined based on the refractive index of a medium adjacent to the thin waveguide layer on the other face. Conduction of a light wave is carried out not only in a thin planar layer, but also by another waveguide structure, and in particular, by a stripped waveguide body. In such a case, the waveguide structure is processed into the shape of a stripped film. It is an important factor for a biosensor that changes in effective refractive indexes N are generated as a result of changes in the medium adjacent to the waveguide layer, and changes in the refractive index and thickness of the waveguide layer itself or an additional layer adjacent to the waveguide layer.

The structure of a biosensor of this system is described in page 4, line 48 to page 14, line 15, and FIGS. 1 to 8 of JP Patent Publication (Kokoku) No. 6-27703 B (1994), and column 6, line 31 to column 7, line 47, and FIGS. 9A and 9B of U.S. Pat. No. 6,829,073.

For example, in one embodiment, there is a structure whereby a waveguide layer comprising a planar thin layer is established on a substrate (e.g. Pyrex (registered trademark) glass). A waveguide layer and a substrate form together a so-called waveguide body. Such a waveguide layer can be a multilayer laminated body such as an oxide layer ($SiO_2$, $SnO_2$, $Ta_2O_5$, $TiO_2$, $TiO_2$—$SiO_2$, $HfO_2$, $ZrO_2$, $Al_2O_3$, $Si_3N_4$, HfON, SiON, scandium oxide, or a mixture thereof) or a plastic layer (e.g. polystyrene, polyethylene, polycarbonate, etc.). For transmission of light into a waveguide layer as a result of total internal reflection, the refractive index of the waveguide layer must be greater than that of the adjacent medium (for example, a substrate, or an additional layer as described later). A diffraction grating is disposed on the surface of the waveguide layer or in the bosom thereof, which faces to a substrate or a measured substance. Such a diffraction grating can be formed in a carrier according to embossing, holography, or other methods. Subsequently, the upper surface of the diffraction grating is coated with a thin waveguide film having a higher refractive index. The diffraction grating has the functions to focus rays of light incident on the waveguide layer, to discharge the mode already introduced into the waveguide layer, or to transmit a portion of the mode in the travel direction and reflect a portion thereof. The grating area of the waveguide layer is covered with an additional layer. Such an additional layer can be a multilayer film, as necessary. This additional layer is able to have the function to carry out selective detection of a substance contained in a measured substance. In a preferred embodiment, a layer having a detection function can be established on the outermost surface of such an additional layer. As such a layer having a detection function, a layer capable of immobilizing physiologically active substances can be used.

In another embodiment, it is also possible to adopt a structure whereby an array of diffraction grating waveguides is incorporated into wells of a microplate (JP Patent Publication (Kohyo) No. 2007-501432 A). That is to say, if such diffraction grating waveguides are aligned in the form of an array at the bottoms of wells of a microplate, the screening of a drug or chemical substance can be carried out at a high throughput.

In order to detect physiologically active substances existing on the upper layer (detection area) of a diffraction grating waveguide, the diffraction grating waveguide detects incident light and reflected light, so as to detect changes in refractive properties. For this purpose, one or more light sources (e.g. laser or diode) and one or more detectors (e.g. a spectrometer, a CCD camera, or other light detectors) can be used. As a method of measuring changes in refractive indexes, there are two different operational modes, namely, spectroscopy and an angle method. In spectroscopy, broadband beam used as incident light is transmitted to a diffraction grating waveguide, and reflected light is gathered, followed by a measurement with a spectrometer, for example. By observing the spectrum position of a resonant wavelength (peak), changes in refractive indexes on the surface of the diffraction grating waveguide or a periphery thereof, namely, a bond can be measured. On the other hand, in an angle method, light of a nominally single wavelength is gathered such that it generates a certain range of irradiation angle, and it is directed into the diffraction grating waveguide. The reflected light is measured with a CCD camera or other types of light detectors. By measuring the position of a resonance angle reflected by the diffraction grating wavelength, changes in refractive indexes on the surface of the diffraction grating waveguide or a periphery thereof, namely, a bond can be measured.

The present invention will be further specifically described in the following examples. However, the examples are not intended to limit the scope of the present invention.

Examples

Hereafter, preferable embodiments for implementing the present invention are described in detail by way of examples with reference to the attached figures. Embodiments shown in the figures are merely representative examples of the substances or methods according to the present invention, and these embodiments are not intended to narrow the scope of the present invention.

FIG. 1 schematically shows the biosensor of the present invention. The biosensor of the present invention comprises a reaction region 4, an assay apparatus 9, and a gold thin-film substrate 2 therebetween. When the assay apparatus 9 is an SPR assay apparatus, a prism 3 used for SPR assay is provided between the reaction region 4 and the assay apparatus 9. In the reaction region 4, an immobilization region 10 can be spatially isolated from an immobilization region 11 using, for example, a micro-fluid path.

A pellet of Zeonex (Zeon Chemicals) was melted at 240° C., and the resulting molten product was applied to an injection mold to prepare a substrate having a length of 8 mm, a width of 120 mm, and a height of 1.5 mm. The substrate was mounted in a hermetically sealed aluminum container having a length of 30 mm, a width of 130 mm, and a depth of 10 mm. This aluminum container was immobilized on the inner cup of a spin coater equipped with a hermetically sealed inner cup (Model: SC408, manufactured by Nanotech), in such a manner that the gold surface substrate was located at a position 135 mm from the center and the tangential direction of a circular arc became the longitudinal axis. A solution of 0.2% 12-hydroxystearic acid in ethanol (100 μl) was added dropwise onto the substrate, using a micropipette, so that the entire surface of the gold surface substrate was coated with coating solution A. The aluminum container was hermetically sealed, allowed to stand for 30 seconds, and then rotated at 200 rpm for 60 seconds. A sputtering film was provided on the substrate using a parallel plate 6-inch sputtering apparatus (SH-550, Ulvac) to a thickness of gold of 50 nm to prepare a gold thin-film substrate 2.

The gold thin-film substrate 2 was treated with a Model-208 UV-ozone cleaning system (TECHNOVISION INC.) for 30 minutes, a solution of 5.0 mM 11-hydroxy-1-undecanethiol in ethanol:water (80:20) was brought into contact with a metal film, and the surface of the substrate was treated at 25° C. for 18 hours. Thereafter, the substrate was washed five times with ethanol, once with a mixed solvent of ethanol/water, and then five times with water.

Subsequently, the 11-hydroxy-1-undecanethiol-coated surface was brought into contact with a solution containing 10% by mass of epichlorohydrin (solvent: a 1:1 mixture of 0.4 M sodium hydroxide and diethylene glycol dimethyl ether), and the reaction was allowed to proceed in a shaking incubator at 25° C. for 4 hours. The surface was washed twice with ethanol and five times with water.

Subsequently, 4.5 ml of 1 M sodium hydroxide solution was added to 40.5 ml of an aqueous solution containing 25% by mass of dextran (T500, Phamiacia), and the resulting solution was brought into contact with the epichlorohydrin-treated surface. Subsequently, the resultant was incubated in a shaking incubator at 25° C. for 20 hours. The surface was washed ten times with water at 50° C.

Subsequently, a mixture of 3.5 g of bromoacetic acid dissolved in 27 g of 2 M sodium hydroxide solution was brought into contact with the dextran-treated surface, and the resultant was incubated in a shaking incubator at 28° C. for 16 hours. The surface was washed with water, and the above-described procedure was repeated once to prepare a hydrophilic film 1.

A solution containing 0.4 M EDC and 0.1 M NHS was injected into a hydrophilic membrane 1 in the reaction region 4, and the resultant was allowed to stand for 7 minutes. The resultant was washed with PBS buffer (pH 7.4), a solution containing 1.0 mg/ml phosphorylated p38 protein 5 (Calbiochem) in acetate buffer (pH 5.5, containing 10 μM of a p38 inhibitor, SB203580) was injected, and the resultant was allowed to stand for 15 minutes to immobilize the p38 protein 5 at the immobilization region 10. p38 protein is a phosphorylating enzyme that phosphorylates a serine or threonine residue of a protein or peptide. The resultant was washed with PBS buffer (pH 7.4), ethanolamine was injected thereinto, the resultant was allowed to stand for 7 minutes, 10 mM NaOH was further injected thereinto, and the resultant was then allowed to stand for 1 minute. The resultant was washed with PBS buffer (pH 7.4), the SPR signal value was measured, and the amount of change relative to a baseline was used to designate the immobilization amount.

At the time of coupling of proteins, acetate buffer (pH 5.5) containing 10 μM SB203580 which is an inhibitor, was used for the following reasons. When an inhibitor is bound to an active site, the protein structure of p38 is maintained in a relatively stable manner (Analytical Biochemistry vol 325, 126-136, 2004).

Subsequently, the anti-phospho-Ser/Thr (mixed mouse monoclonal IgG) antibody 8 (0.1 mg/ml, 70 μl, Funakoshi) was injected into the reaction region 4, and immobilized at the immobilization region 11 in the same manner as described above. The antibody 8 is used for an antigen-antibody reaction involving the use of an antigen as a sensing molecule. When a hormone is a sensing molecule, a molecule that specifically binds to the hormone can be used. When DNA is a sensing molecule, a molecule that specifically binds to the DNA of interest can be used.

Figure 2:
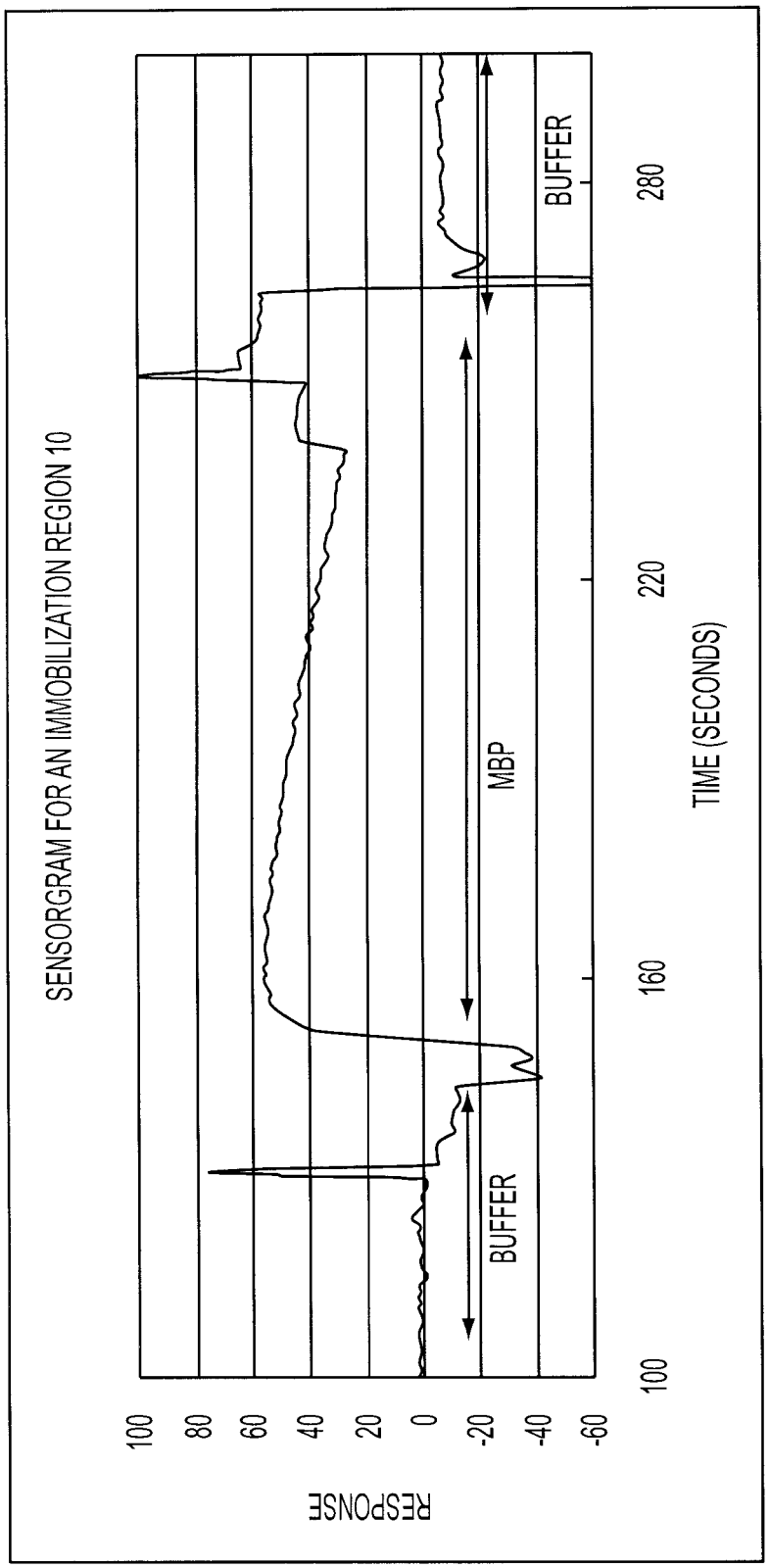
FIG. 2 shows a sensorgram for an immobilization region 10 when a test substance is injected.
Figure 3:
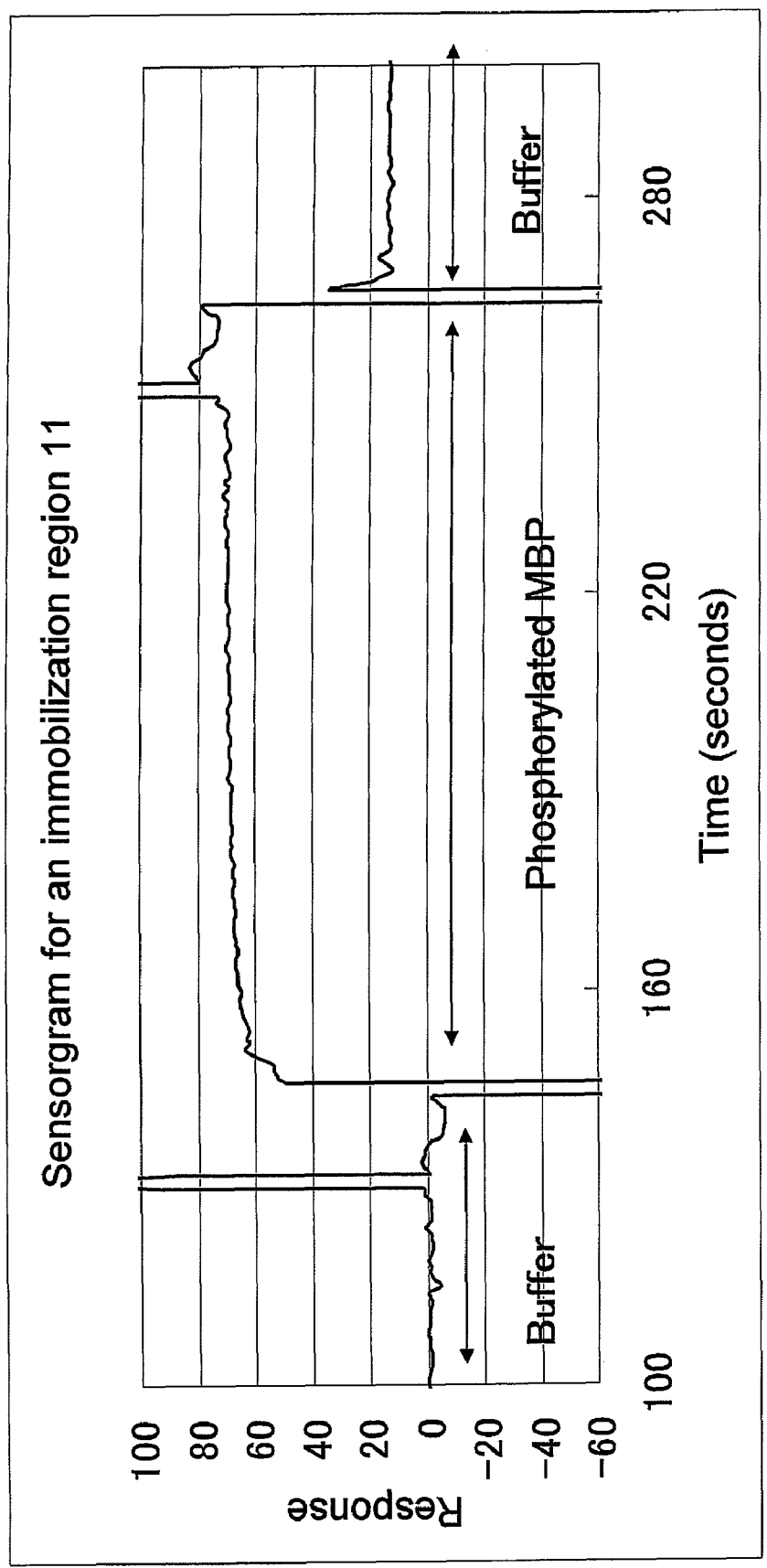
FIG. 3 shows a sensorgram for an immobilization region 11 when a test substance is injected.

MBP6 (myelin basic protein, Wako Pure Chemical Industries, Ltd.) which was dissolved in buffer containing 1×PBS, 10 μM ATP, 1 mM $MgCl_2$ and 5% DMSO at a concentration of 100 ng/ml was injected into the reaction region, and SPR signals at the immobilization regions 10 and 11 were assayed. FIG. 2 shows a sensorgram for the immobilization region 10, and FIG. 3 shows a sensorgram for the immobilization region 11. MBP7, which is a reaction product phosphorylated by p38 protein, is recognized by a phosphorylation-specific antibody in the immobilization region 11 and then detected as a binding signal.

Figure 4:
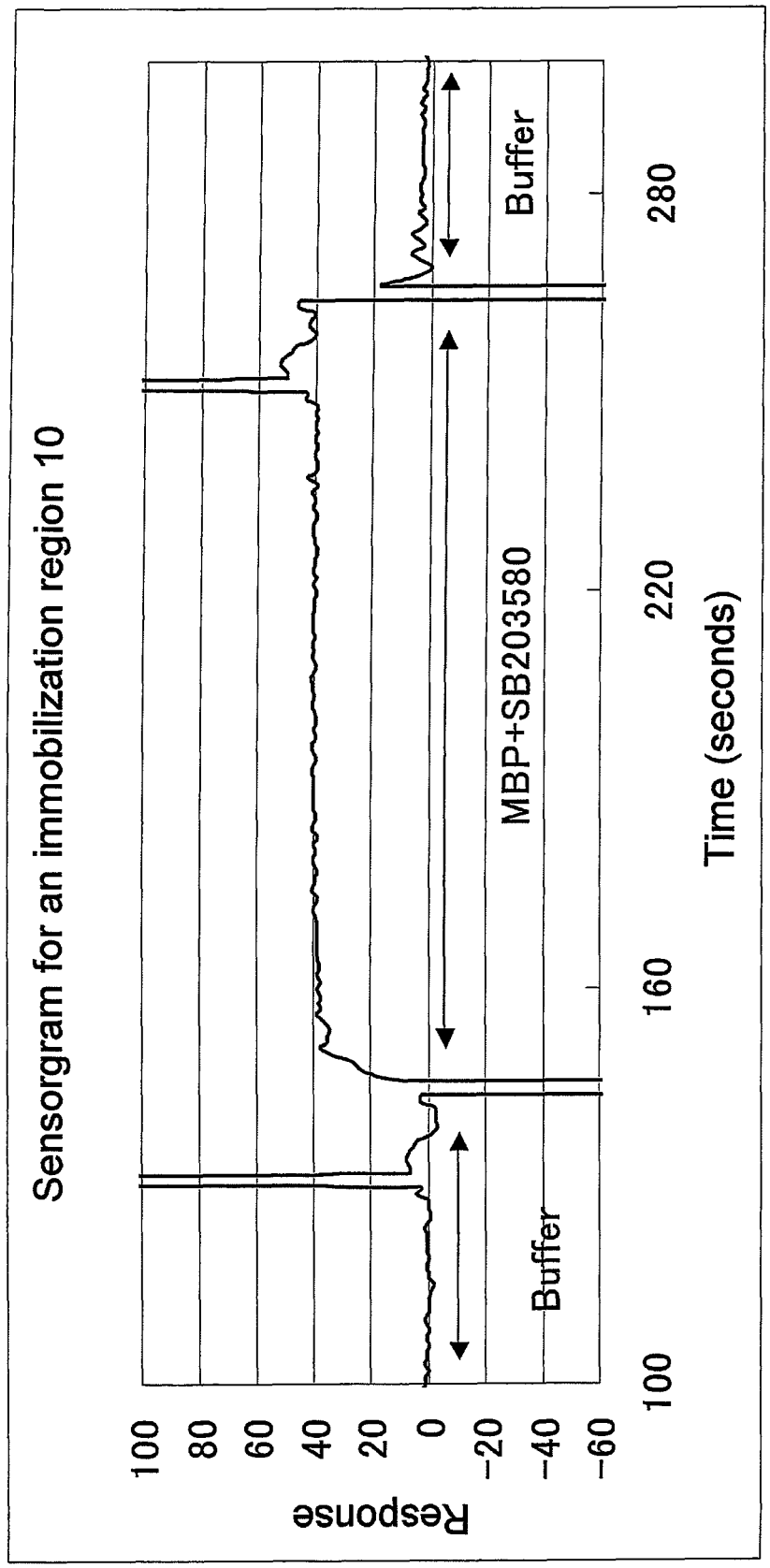
FIG. 4 shows a sensorgram for an immobilization region 10 when a test substance and an inhibitor are injected.
Figure 5:
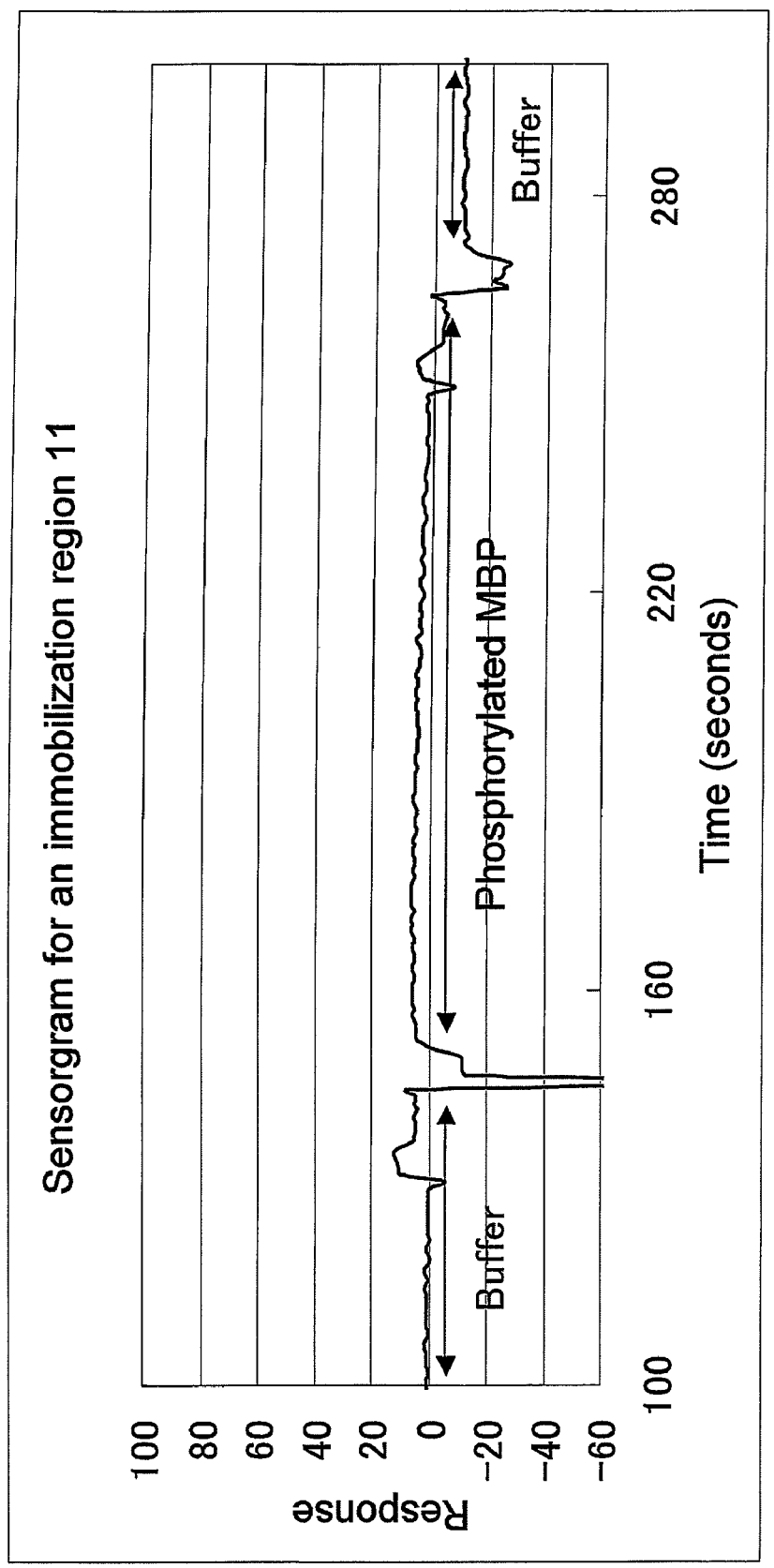
FIG. 5 shows a sensorgram for an immobilization region 11 when a test substance and an inhibitor are injected.

This reaction region was washed with 1×PBS, MBP (myelin basic protein, Wako Pure Chemicals, Industries. Ltd.) which was dissolved in buffer comprising 1× PBS, 10 μM ATP, 1 mM $MgCl_2$, and 5% DMSO at a concentration of 100 ng/ml and 1 μM of an inhibitor, SB203580 (Funakoshi), were simultaneously injected thereinto, and SPR signals at the immobilization regions 10 and 11 were assayed. FIG. 4 shows a sensorgram for the immobilization region 10, and FIG. 5 shows a sensorgram for the immobilization region 11. A signal corresponding to binding of a compound is observed in the immobilization region 11. Since enzyme activity is inhibited by SB203580, phosphorylated MBP is not generated, and a binding signal is not detected at the immobilization region 11. Thus, binding of an inhibitor and inhibition of the reaction can be simultaneously detected according to the present invention. When inhibitor is screened using an SPR apparatus, a compound that often undergoes binding but does not inhibit activity is disadvantageously detected as a hit inhibitor (i.e., a false positive). According to the present invention, a false positive would not be detected, and true positive results can be selectively obtained within a short period of time.

The above examples can be applied in the manner, for example, as shown in FIG. 6. Specifically, a reaction product 7 obtained from a substrate 6 with the aid of an enzyme 5 via an enzyme reaction can activate an enzyme 13 immobilized at an immobilization region 11. The activated enzyme 13 generates a reaction product 15 from a substrate 14, and the reaction product 15 can be captured with the aid of a specific binding molecule 8 to assay the abundance thereof. Screening with the addition of an inhibitor to a series of reaction system enables simultaneous detection of information regarding an inhibitory pathway or inhibition specificity and binding.

The invention claimed is:

1. A biosensor for detecting a test molecule specifically binding to a physiologically active substance, which comprises:
   (1) (a) a first reaction region on which the physiologically active substance has been immobilized for performing a binding reaction between the physiologically active substance and the test molecule and a physiologically active reaction caused by the physiologically active substance, and (b) a second reaction region on which a molecule that specifically binds to a reaction product resulting from the physiologically active reaction has been immobilized for performing a binding reaction between the reaction product and the molecule that specifically binds to the reaction product, in the same area; and
   (2) an assay region for detecting changes in the binding reaction in the first reaction region and in the binding reaction in the second reaction region, the assay region being provided in such a way that the assay region can monitor the binding reactions in the first and second reaction regions by using surface plasmon resonance (SPR) assay, wherein
   the reaction product moves spontaneously from the first reaction region to the second reaction region by diffusion.

2. The biosensor according to claim 1, which comprises two or more first reaction regions.

3. The biosensor according to claim 1, which comprises two or more second reaction regions.

4. The biosensor according to claim 1, wherein the first reaction region and the second reaction region are separated from each other by an air gap.

5. The biosensor according to claim 4, wherein the air gap is movable air gap.

6. The biosensor according to claim 1, wherein the changes in the binding reaction in the first reaction region and in the binding reaction in the second reaction region are changes in dielectric constant.

7. The biosensor according to claim 1, wherein the assay region includes a waveguide, and the first and second regions are on the waveguide.

* * * * *